(12) United States Patent
Hirsch et al.

(10) Patent No.: US 7,972,599 B2
(45) Date of Patent: Jul. 5, 2011

(54) IMMUNOMODULATION OF INFLAMMATORY CONDITIONS UTILIZING FOLLISTATIN-LIKE PROTEIN-1 AND AGENTS THAT BIND THERETO

(75) Inventors: Raphael Hirsch, Pittsburgh, PA (US); Anthony D. Marinov, Munhall, PA (US); David C. Wilson, Monroeville, PA (US)

(73) Assignee: University of Pittsburgh of the Commonwealth System of Higher Education

( * ) Notice: Subject to any disclaimer, the term of this patent is extended or adjusted under 35 U.S.C. 154(b) by 56 days.

(21) Appl. No.: 11/688,779

(22) Filed: Mar. 20, 2007

(65) Prior Publication Data

US 2007/0253962 A1 Nov. 1, 2007

Related U.S. Application Data

(60) Provisional application No. 60/784,020, filed on Mar. 20, 2006.

(51) Int. Cl.
*A61K 39/395* (2006.01)
(52) U.S. Cl. .................................. 424/145.1; 424/130.1
(58) Field of Classification Search .................. None
See application file for complete search history.

(56) References Cited

U.S. PATENT DOCUMENTS

| | | | |
|---|---|---|---|
| 4,946,778 | A | 8/1990 | Ladner et al. |
| 5,605,690 | A | 2/1997 | Jacobs et al. |
| 6,410,232 | B1 | 6/2002 | Holtzman |
| 2005/0202421 | A1* | 9/2005 | Hirsch et al. ...................... 435/6 |

FOREIGN PATENT DOCUMENTS

| | | |
|---|---|---|
| WO | WO-94/06476 A1 | 3/1994 |
| WO | WO-2004/018522 A2 | 3/2004 |
| WO | WO-2004/018522 A3 | 3/2004 |
| WO | WO-2005/005471 A2 | 1/2005 |
| WO | WO-2005/005471 A3 | 1/2005 |
| WO | WO-2005/032328 A2 | 4/2005 |
| WO | WO-2005/032328 A3 | 4/2005 |

OTHER PUBLICATIONS

The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock. see pp. 1-5.*
Standen et al. (N Engl J Med 2000, 343:447-448).*
Aggarwal, S. et al. (Jan. 17, 2003). "Interleukin-23 Promotes a Distinct CD4 T Cell Activation State Characterized by the Production of Interleukin-17," *Journal of Biological Chemistry* 278(3):1910-1914.
Bettelli, E. et al. (May 11, 2006). "Reciprocal Developmental Pathways for the Generation of Pathogenic Effector $T_H17$ and Regulatory T Cells," *Nature* 441:235-238.
Cole, S.P.C. et al. (1985). "The EBV-Hybridoma Technique and Its Application to Human Lung Cancer," *in Monoclonal Antibodies and Cancer Therapy*, pp. 77-96.
Constantinescu, C.S. et al. (1998). "Antibodies Against IL-12 Prevent Superantigen-Induced and Spontaneous Relapses of Experimental Autoimmune Encephalomyelitis," *J. Immunol.* 161:5097-5104.
Cote, R.J. et al. (Apr. 1983). "Generation of Human Monoclonal Antibodies Reactive with Cellular Antigens," *Proc. Natl. Acad. Sci. USA* 80:2026-2030.
Ehara, Y. et al. (Nov.-Dec. 2004). "Follistatin-Related Protein Gene (*FRP*) is Expressed in the Synovial Tissues of Rheumatoid Arthritis, But its Polymorphisms are not Associated with Genetic Susceptibility," *Clin. Exp. Rheumatol.* 22:707-712.
GenBank Accession No. BC000055 updated Jul. 15, 2006, located at <http://www.ncbi.nlm.nih.gov/entrez/viewer.fcgi?db=nuccore&id=33990756>, last visited on Aug. 8, 2007, four pages.
GenBank Accession No. BC028921 updated Jul. 15, 2006, located at <http://www.ncbi.nlm.nih.gov/entrez/viewer.fcgi?db=nuccore&id=208100326>, last visited Aug. 8, 2007, three pages.
Hambrock, H.O. et al. (Mar. 19, 2004, e-pub. Dec. 30, 2003). "Structural Characterization of TSC-36/Flik: Analysis of Two Charge Isoforms," *Journal of Biological Chemistry* 279(12):11727-11735.
Hardy, S. et al. (Mar. 1997). "Construction of Adenovirus Vectors Through Cre-*lox* Recombination," *Journal of Virology* 71(3):1842-1849.
Honorati, M.C. et al. (2001). "High in vivo Expression of Interleukin-17 Receptor in Synovial Endothelial Cells and Chondrocytes From Arthritis Patients," *Rheumatology* 40:522-527. Hwang, S.Y. et al. (2004). "IL-17 Induces Production of IL-6 and IL-8 in Rheumatoid Arthritis Synovial Fibroblasts via NF-κB- and PI3-Kinase/Akt-Dependent Pathways," *Arthritis Res. Ther.* 6(2):R120-R128.
International Search Report mailed Nov. 15, 2007, for PCT Application No. PCT/US2007/064441, filed Mar. 20, 2007, eight pages.
Ivanov, I.I. et al. (Sep. 22, 2006). "The Orphan Nuclear Receptor RORγt Directs the Differentiation Program of Proinflammatory IL-17+ T Helper Cells," *Cell* 126:1121-1133.
Johnston, I.M.P. et al. (Nov. 9, 2000). "Regulation of a Multigenic Invasion Programme by the Transcription Factor, AP-1: Re-Expression of a Down-Regulated Gene, TSC-36, Inhibits Invasion," *Oncogene* 19:5348-5358.
Kawabata, D. et al. (Feb. 2004). "Ameliorative Effects of Follistatin-Related Protein/TSC-36/FSTL1 on Joint Inflammation in a Mouse Model of Arthritis," *Arth. Rheum.* 50(2):660-668.

(Continued)

*Primary Examiner* — Sharon Wen
(74) *Attorney, Agent, or Firm* — Baker Botts LLP

(57) ABSTRACT

Follistatin-like protein (FSTL-1) is a secreted glycoprotein of unknown function, first isolated from mouse osteoblastic cells as a transforming growth factor-β1-inducible gene. The inventors have discovered that FSTL-1 is a proinflammatory mediator. As such, the invention provides for composition and methods of using agents that bind to FSTL-1 to modulate various types of inflammation (e.g., autoimmune diseases). Inhibitors and antagonists of FSTL-1, particularly antibodies or antibody fragments, may be used to treat conditions related to inflammation, such as arthritis. In addition, the inventors have discovered that FSTL-1 has a role in the Th17 pathway. Accordingly, the invention provides for compositions and methods of using agents which bind to FSTL-1 to modulate the generation of Th17 cells. Such agents are useful for delaying development of and treating diseases associated with undesired production of Th17 cells, such as autoimmune diseases. Furthermore, since FSTL-1 is a proinflammatory mediator with a role in cancer, the invention provides for compositions and methods of using a pharmaceutical composition of FSTL-1 to delay development of or treat cancer.

9 Claims, 9 Drawing Sheets

OTHER PUBLICATIONS

Kim, H.-R. (2007). "Up-Regulation of IL-23p19 Expression in Rheumatoid Arthritis Synovial Fibroblasts by IL-17 Through PI3-Kinase-, NF-κB- and p38 MAPK-Dependent Signalling Pathways," *Rheumatology* 46:57-64.

Kohler, G. et al. (Aug. 7, 1975). "Continuous Cultures of Fused Cells Secreting Antibody of Predefined Specificity," *Nature* 256:495-497.

Kolls, J.K. et al. (Oct. 2004). "Interleukin-17 Family Members and Inflammation," *Immunity* 21:467-476.

Kotake, S. et al. (May 1999). "IL-17 in Synovial Fluids from Patients with Rheumatoid Arthritis is a Potent Stimulator of Osteoclastogenesis," *J. Clin. Invest.* 103(9):1345-1352.

Kozbor, D. et al. (1983). "The Production of Monoclonal Antibodies from Human Lymphocytes," *Immunology Today* 4(3):72-79.

Leonard, J.P. (Jan. 1, 1995). "Prevention of Experimental Autoimmune Encephalomyelitis by Antibodies Against Interleukin 12," *J. Exp. Med.* 181(1):381-386.

Lubberts, E. et al. (2001). "IL-1-Independent Role of IL-17 in Synovial Inflammation and Joint Destruction During Collagen-Induced Arthritis," *J. Immunol.* 167:1004-1013.

Mashimo, J. et al. (Feb. 26, 1997). "Decrease in the Expression of a Novel TGF β1-Inducible and *ras*-Recision Gene, TSC-36, in Human Cancer Cells," *Cancer Lett.* 113(1,2):213-219.

Miyamae, T. et al. (May 2005). "Over-Expression of Follistatin-Like Protein Exacerbates Collagen Induced Arthritis," *Molecular Therapy* 11(1-Suppl.1):S264, Abstract No. 682.

Miyamae, T. et al. (Oct. 1, 2006). "Follistatin-Like Protein-1 Is a Novel Proimflammatory Molecule," *Journal of Immunolgy* 177(7):4758-4762.

Mohan, A. et al. (Oct. 2001). "Effect of Cytokines and Growth Factors on the Secretion of Inhibin A, Activin A and Follistatin by Term Placental Villous Trophoblasts in Culture," *Eur. J. Endocrinol.* 145:505-511.

Morrison, S.L. et al. (Nov. 1984). "Chimeric Human Antibody Molecules: Mouse Antigen-Binding Domains with Human Constant Region Domains," *Proc. Natl. Acad. Sci.* 81:6851-6855.

Nakae, S. et al. (2003). "Suppression of Immune Induction of Collagen-Induced Arthritis in IL-17-Deficient Mice," *J. Immunol.* 171:6173-6177.

Neuberger, M.S. et al. (Dec. 13, 1984). "Recombinant Antibodies Possessing Novel Effector Functions," *Nature* 312:604-608.

Ohashi, T. et al. (Nov. 1997). "TSC-36 (Follistatin-Related Polypeptide) Gene Expression in Estrogen Receptor Positive Osteoblastic Cell Line, CDO7F," *Calcif. Tissue Int.* 61:400-403.

Okabayashi, K. et al. (Jan. 8, 1999). "cDNA Cloning and Distribution of the *Xenopus* Follistatin-Related Protein," *Biochem. Biophys. Res. Commun.* 254(1):42-48.

Oppmann, B. et al. (Nov. 2000). "Novel p19 Protein Engages IL-12p40 to Form a Cytokine, IL-23, with Biological Activities Similar as Well as Distinct from IL-12," *Immunity* 13:715-725.

Overbergh, L. et al. (Mar. 2003). "The Use of Real-Time Reverse Transcriptase PCR for the Quantification of Cytokine Gene Expression," *Journal of Biomolecular Techniques* 14(1):33-43.

Segal, B.M. et al. (Feb. 16, 1998). "An Interleukin (IL)-10/IL-12 Immunoregulatory Circuit Controls Susceptibility to Autoimmune Disease," *J. Exp. Med.* 187(4):537-546.

Shibanuma, M. et al. (Oct. 1993). "Cloning from a Mouse Osteoblastic Cell Line of a Set of Transforming-Growth-Factor-β1-Regulated Genes, One of Which Seems to Encode a Follistatin-Related Polypeptide," *Eur. J. Biochem.* 217(1):13-19.

Sumitomo, K. et al. (Jul. 3, 2000). "Expression of a TGF-β1 Inducible Gene, TSC-36, Causes Growth Inhibition in Human Lung Cancer Cell Lines," *Cancer Lett.* 155(1):37-46.

Takeda, S-I. et al. (Apr. 4, 1985). "Construction of Chimaeric Processed Immunoglobulin Genes Containing Mouse Variable and Human Constant Region Sequences," *Nature* 314:452-454.

Tanaka, M. et al. (1998). "Cloning of Follistatin-Related Protein as a Novel Autoantigen in Systemic Rheumatic Diseases," *International Immunology* 10(9):1305-1314.

Tanaka, M. et al. (Jan. 2003). "Potential Preventive Effects of Follistatin-Related Protein/TSC-36 on Joint Destruction and Antagonistic Modulation of its Autoantibodies in Rheumatoid Arthritis," *International Immunoogy* 15(1):71-77.

Thornton, S. et al. (Nov. 2002). "DNA Microarray Analysis Reveals Novel Gene Expression Profiles in Collagen-Induced Arthritis," *Clin. Immunol.* 105(2):155-168.

Trojan, L. et al. (Jan.-Feb. 2005). "Identification of Metastasis-Associated Genes in Prostate Cancer by Genetic Profiling of Human Prostate Cancer Cell Lines," *Anticancer Res.* 25(1A):183-192.

Veldhoen, M. et al. (Feb. 2006). "TGFβ in the Context of an Inflammatory Cytokine Milieu Supports De Novo Differentiation of IL-17-Producing T Cells," *Immunity* 24:179-189.

Zhou, J. et al. (Mar. 6, 2006). "Identification of a Follistatin-Related Protein from the Tick *Haemaphysalis longicornis* and Its Effect on Tick Oviposition," *Gene* 372:191-198.

* cited by examiner

IMMUNOMODULATION OF INFLAMMATORY CONDITIONS UTILIZING FOLLISTATIN-LIKE PROTEIN-1 AND AGENTS THAT BIND THERETO

CROSS-REFERENCE TO RELATED APPLICATIONS

This application claims priority to U.S. Provisional Patent Application 60/784,020 which was filed on Mar. 20, 2006, the contents of which are hereby incorporated by reference in its entirety.

FIELD OF THE INVENTION

The present invention relates to the immunomodulation of inflammatory conditions by using Follistatin-like Protein-1 (FSTL-1) and agents that bind to FSTL-1. The invention provides for antagonists to FSTL-1, for example, neutralizing antibodies, which are useful for the prophylaxis and treatment of inflammatory conditions. The invention further provides for immunomodulation of inflammatory conditions such as cancer by using FSTL-1. The invention further provides for the immunomodulation of conditions related to Th17 cells and the Th17 regulatory pathway.

BACKGROUND OF THE INVENTION

Follistatin-like Protein-1 (FSTL-1), also known as FRP and TSC-36, is an extracellular glycoprotein belonging to the BM-40/SPARC/osteonectin family of proteins containing both extracellular calcium-binding and follistatin-like domains. See e.g., U.S. Pat. No. 6,410,232. FSTL-1 was originally cloned from an osteoblastic cell line as a TGF-β inducible gene. M. Shibanuma et al., *Eur J Biochem* 217, 13 (1993). The protein occurs in two isoforms resulting from differential sialylation. FSTL-1 has been detected in the medium of all osteosarcoma and chondrosarcoma cell lines, and in some cells of the fibroblast lineage. In mice, the highest expression of FSTL-1 has been observed in the lung. J. Mashimo et al., *Cancer Lett* 113, 213 (1997).

The action of FSTL-1 is unclear, and both proliferative and anti-proliferative effects have been reported. It is thought that FRP may play a role in neuralization during embryogenesis and its expression is upregulated by estrogen. See K. Okabayashi et al., *Biochem Biophys Res Commun* 254, 42 (Jan. 8, 1999) and T. Ohashi et al., *Calcif Tissue Int* 61, 400 (November 1997). In contrast to other BM-40 family members, the extracellular calcium-binding domain of FSTL-1 is non-functional, suggesting that, despite its sequence homology to BM-40, it has evolved clearly distinct properties. H. O. Hambrock et al., *Journal of Biological Chemistry* 279, 11727 (Mar. 19, 2004). Analysis of prostate cancers has revealed that over-expression of FSTL-1 may be associated with higher metastatic potential. L. Trojan et al., *Anticancer Res* 25, 183 (January-February, 2005). In contrast, FSTL-1 expression has been extinguished in v-ras-transformed rat fibroblasts, and transfection of FSTL-1 into these cells inhibited in vitro invasion and led to growth inhibition in human lung cancer cells. See I. M. Johnston et al., *Oncogene* 19, 5348 (Nov. 9, 2000) and K. Sumitomo et al., *Cancer Lett* 155, 37 (Jul. 3, 2000).

In 1998, Tanaka et al. cloned FSTL-1 from rheumatoid arthritis (RA) synovial tissue and demonstrated anti-FSTL-1 antibodies in the serum and synovial fluid of RA patients. M. Tanaka et al., *International Immunology* 10, 1305 (1998). In addition, it has previously been shown that FSTL-1 is highly-upregulated in the joints during the acute phase of collagen-induced arthritis (CIA), most prominently at the junction of synovium and eroding bone, suggesting a role in joint destruction. S. Thornton et al., *Clin Immunol* 105, 155 (2002). Furthermore, FSTL-1 expression in RA synovium has also been observed.

Tanaka et. al. recently reported that administration of human FSTL-1 to Balb/c mice with antibody-induced arthritis ameliorated disease, possibly by reducing synovial production of matrix metalloproteinases. See D. Kawabata et al., *Arth Rheum* 50, 660 (February, 2004) and M. Tanaka et al., *International Immunology* 15, 71 (January, 2003). The effect was mild and may be a consequence of using the human protein or using a mouse with a predominant Th2 phenotype (Balb/c). However, this finding has not been reproduced in the CIA model, and polymorphisms in FSTL-1 were not found to be associated with genetic susceptibility to RA. Y. Ehara et al., *Clin Exp Rheumatol* 22, 707 (November-December, 2004).

Based on the ability to bind various cell growth factors and extracellular matrices, follistatin modules have been proposed as regulators of growth factors and/or cytokines. See K. Sumitomo et al., *Cancer Lett* 155, 37 (Jul. 3, 2000).

All references cited herein are hereby incorporated by reference in their entirety.

BRIEF SUMMARY OF THE INVENTION

The invention provides for compositions and methods for immunomodulation of inflammatory conditions by using FSTL-1 protein and agents that bind to FSTL-1. Compositions and methods using agents that bind to FSLT-1 (e.g., antibodies to FSTL-1) are useful for delaying the development of and/or treating inflammatory conditions. In one aspect, the inflammatory condition is autoimmune disease. In addition, compositions and methods using FSLT-1 protein are useful for delaying the development of and/or treating certain inflammatory conditions, such as cancer.

Accordingly, in one aspect, the invention is a composition comprising an antagonist to FSTL-1 wherein the antagonist is capable of modulating the activity of FSTL-1 in an individual. In one embodiment, the activity of FSTL-1 has a proinflammatory effect in an individual. In another embodiment, the proinflammatory effect is the increased expression of the proinflammatory cytokines TNF-α, IL-6, TGF-β, and IL-17 in the individual. In another embodiment, the modulation is a decrease in the proinflammatory effect of FSTL-1. In another embodiment, the antagonist is an antibody or a fragment thereof to FSTL-1. In another embodiment, the antibody is a neutralizing antibody. In another embodiment, the neutralizing antibody ameliorates at least one symptom associated with autoimmune disease when administered to an individual. In another embodiment, the autoimmune disease is arthritis.

In another embodiment, the compositions above further include a pharmaceutically acceptable excipient. In another embodiment, in the compositions above, the antagonist is selected from the group consisting of an antibody or fragment thereof, a small molecule, a soluble FSTL-1 receptor, an antisense RNA or RNAi. In another embodiment, in the compositions above, the modulation decreases the induction of Th17 cells in an individual.

In another aspect, the invention provides for methods for treating a condition associated with inflammation in an individual by administering to the individual an agent that modulates FSTL-1 activity in an amount effective to modulate the activity of FSTL-1. In one embodiment, the condition associated with inflammation is autoimmune disease. In another embodiment, the autoimmune disease is arthritis. In another embodiment, the autoimmune disease is selected from the group consisting of arthritis, lupus, diabetes, multiple sclerosis, asthma, inflammatory bowel disease, scleroderma, and vasculitis. In another embodiment, the condition associated with inflammation is cancer. In another embodiment, the condition associated with inflammation is selected from the group consisting of arthritis, asthma, septic shock, diabetes and autoimmunity.

In another aspect, the invention provides for methods for treating a condition characterized by inflammation in an individual by administering to the individual an effective amount of any one of the composition above such that FSTL-1 activity is antagonized. In one embodiment, the condition characterized by inflammation is arthritis.

In another aspect, the invention provides for methods for inducing an inflammatory response in an individual in need thereof by administering to the individual a composition comprising FSTL-1 or a fragment thereof in an amount effective for inducing one or more proinflammatory cytokine. In one embodiment, there is one or more cancerous cell in the individual. In another embodiment, the proinflammatory cytokine is selected from the group consisting of IL-6, TNF-α, TGF-β, and IL-17.

In another aspect, the invention provides for methods for treating a condition characterized by inflammation in an individual by administering to the individual an effective amount of an antagonist to FSTL-1 such that FSTL-1 activity is antagonized wherein the antagonist is selected from the group consisting of an antibody, a small molecule, a soluble FSTL-1 receptor, an antisense RNA and RNAi.

In another aspect, the invention provides for methods for ameliorating the symptoms associated with autoimmune disease comprising administering the individual a sufficient amount of an antagonist to FSTL-1 to inhibit or decrease the induction of Th17 cells to the extent that would otherwise give rise to an autoimmune response.

DETAILED DESCRIPTION OF THE INVENTION

Figure 1:
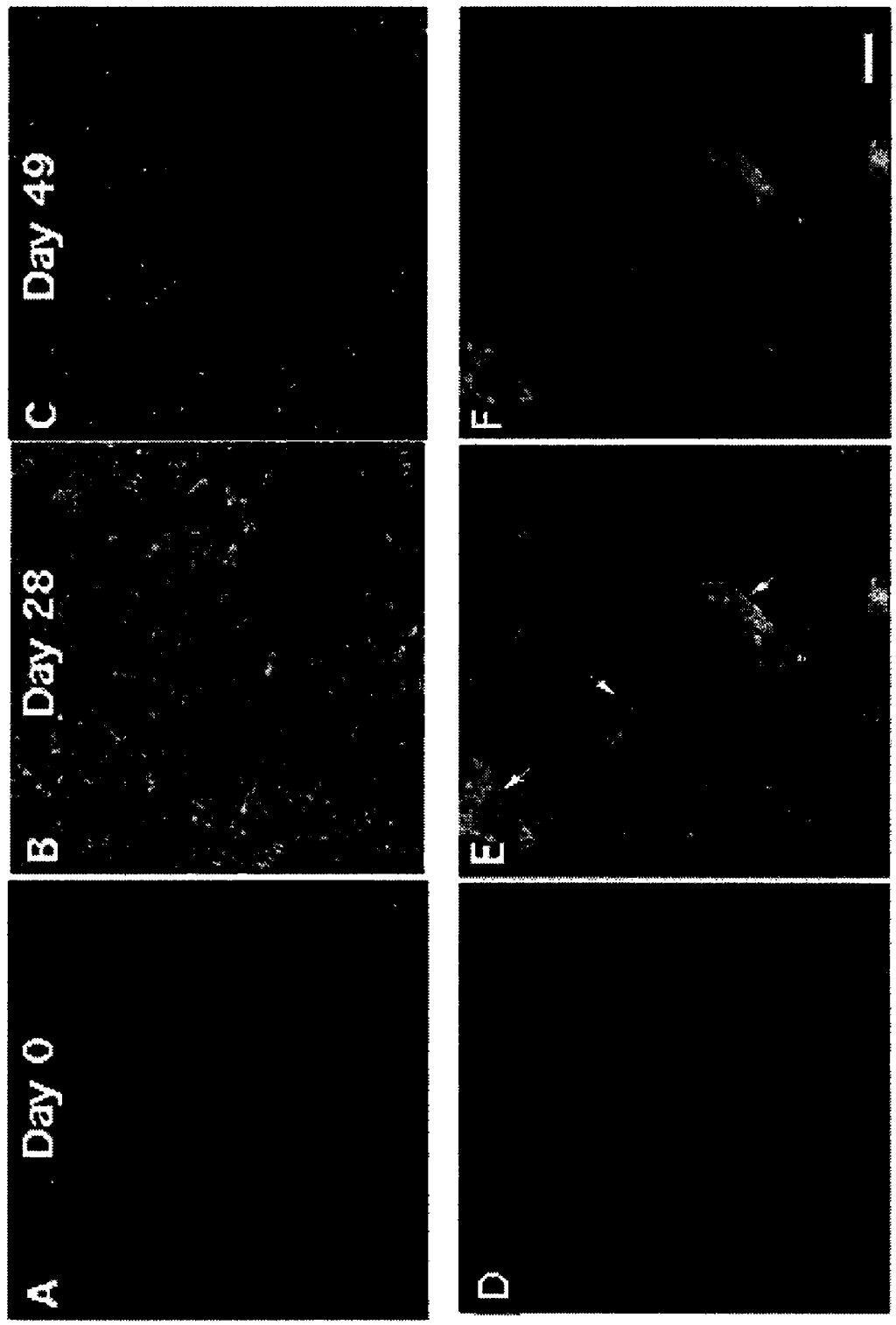
FIG. 1 shows that FSTL-1 is overexpressed in fibroblast-like synoviocytes in early collagen-induced arthritis (CIA).

The invention provides for immunomodulation of inflammatory conditions by utilizing FSTL-1 protein and agents that bind to FSTL-1. Inflammatory conditions in the context of this invention include autoimmune diseases as well as cancer. Autoimmune diseases can be modulated by using an agent which is antagonist for FSTL-1. Autoimmune diseases can also be modulated by using an amount of an agent which is an antagonist for FSTL-1 that is sufficient to effect a reduction in the number and/or the functionality of Th17 cells. Inflammatory conditions such as cancer can be immunomodulated by utilizing FSTL-1 protein.

General Techniques

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), jointly and individually referred to herein as "Sambrook"); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane (1988) *Antibodies, A Laboratory Manual*, Cold Spring Harbor Publications, New York, and Harlow and Lane (1999) *Using Antibodies: A Laboratory Manual* Cold Spring Harbor Laboratory Press, Cold Spring Harbor, N.Y. jointly and individually referred to herein as "Harlow and Lane"), Beaucage et al. eds., *Current Protocols in Nucleic Acid Chemistry* (John Wiley & Sons, Inc., New York, 2000); and Agrawal, ed., *Protocols for Oligonucleotides and Analogs, Synthesis and Properties* (Humana Press Inc., New Jersey, 1993).

Definitions

An "antagonist" to FSLT-1 refers to any agent that blocks, suppresses or reduces (including significantly) FSTL-1 biological activity, including downstream pathways mediated by FSTL-1 signaling, such as binding to activin and/or elicitation of a cytokine expression.

The term "antagonist" does not imply a specific mechanism of biological action and is deemed to expressly include and encompass all possible pharmacological, physiological, and biochemical interactions with FSTL-1 whether direct or indirect, or whether interacting with FSTL-1, its receptor, or through another mechanism, and its consequences which can be achieved by a variety of different, and chemically divergent, compositions. Exemplary FSTL-1 antagonists include, but are not limited to, an anti-FSTL-1 antibody, an anti-sense molecule directed to an FSTL-1 or FSTL-1 receptor (including an anti-sense molecule directed to a nucleic acid encoding FSTL-1), an FSTL-1 inhibitory compound, an FSTL-1 structural analog, and a dominant-negative mutation of the receptor that binds an FSTL-1. For purpose of the present invention, it will be explicitly understood that the term "antagonist" encompass all the previously identified terms, titles, and functional states and characteristics whereby the FSTL-1 itself, an FSTL-1 biological activity (including but not limited to its proinflammatory ability), or the consequences of the biological activity, are substantially nullified, decreased, or neutralized in any meaningful degree. In some embodiments, an FSTL-1 antagonist binds (physically interact with) FSTL-1 (e.g., an antibody), binds to an FSTL-1 receptor, reduces (impedes and/or blocks) downstream FSTL-1 receptor signaling, and/or inhibits (reduces) the synthesis of IL-1β, TNF-α, and IL-6, or their production or release. In some embodiments, an FSTL-1 antagonist binds (physically interacts with) FSTL-1 (e.g., an antibody), binds to an FSTL-1 receptor, and/or reduces (impedes and/or blocks) downstream FSTL-1 receptor signaling. In other embodiments, an FSTL-1 antagonist binds FSTL-1 and prevents the induction of Th17 cells. Examples of types of FSTL-1 antagonists are provided herein.

An "antibody" (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, humanized antibodies, chimeric antibodies, diabodies linear antibodies, single chain antibodies, multispecific antibodies (e.g., bispecific antibodies) and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody. In some instances, framework region (FR) residues or other residues of the human immunoglobulin replaced by corresponding non-human residues. Furthermore, humanized antibodies may comprise residues which are not found in the recipient antibody or in the donor antibody.

An "individual" is a vertebrate, such as mouse, and is preferably a mammal, more preferably a human. Mammals include, but are not limited to, humans, primates, farm animals, sport animals, rodents and pets.

An "effective amount" of a substance is that amount sufficient to effect beneficial or desired results, including clinical results, and, as such, an "effective amount" depends upon the context in which it is being applied. In the context of administering a composition that modulates an immune response, an effective amount of an agent which is an antagonist to FSTL-1 is an amount sufficient to achieve such a modulation as compared to the immune response obtained when there is no antagonist administered. An effective amount can confer long term benefits of disease modification, such as suppression and/or inhibition of Th17 cells or production of IL-17. An effective amount can be administered in one or more administrations.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, delay or slowing of disease progression, and/or amelioration or palliation of the disease state. "Treatment" can also mean prolonging survival as compared to expected survival if not receiving treatment.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For example of carriers, stabilizers and adjuvants, see Martin, REMINGTON'S PHARM. SCI., 15th Ed. (Mack Publ. Co., Easton (1975)).

Role of FSTL-1 as a Proinflammatory Molecule

The invention is based in part on the discovery that FSTL-1 is a proinflammatory molecule. Thus, inhibiting or antagonizing the expression of FSTL-1 or neutralizing its activity can modulate an inflammatory condition.

FSTL-1 is a secreted glycoprotein of previously unknown function, first isolated from mouse osteoblastic cells as the product of a transforming growth factor-β1-induciblegene. As explained in greater detail in the Examples, the present inventors have discovered that FSTL-1 is overexpressed in fibroblast-like synoviocytes in rheumatoid arthritis (RA) and mouse collagen-induced arthritis (CIA). FSTL-1 expression in the joints is observed mostly in the acute phase of CIA and predominantly in fibroblast-like synoviocytes. Such overexpresssion may lead to secretion of IL-6 by these cells to serve as a proinflammatory signal. In addition, FSTL-1 secreted by these cells might stimulate resident macrophages to secrete proinflammatory cytokines. Further, FSTL-1 may lead to induction of Th17 cells and secretion of IL-17.

As further detailed in the Examples, overexpression of the FSTL-1 gene, or exposure to FSTL-1 protein, induced secretion of IL-1β, TNF-α, and IL-6 from macrophages and IL-17 from T cells. In addition, gene transfer of FSTL-1 to liver upregulated mRNA for these cytokines. Furthermore, in vivo overexpression of FSTL-1 exacerbated CIA.

Accordingly, the present invention provides a role for FSTL-1 activity in the context of inflammation. FSTL-1 secreted by fibroblasts or other cells such as osteoblasts acts upon certain cells such as T cells or macrophages or others to increase production of proinflammatory cytokines such as IL-17, TNF-α and IL-1β. A. Mohan et al., *Eur J Endocrinol* 145, 505 (October 2001). Thus, modulation of inflammatory conditions is effectuated by using FSTL-1 and agents that bind thereto Immunomodulation of Autoimmune Diseases The present invention provides for compositions and methods for immunomodulation of inflammatory conditions. Examples of inflammatory conditions include autoimmune diseases, which include but are not limited to: arthritis, lupus, diabetes, multiple sclerosis, asthma, inflammatory bowel disease, scleroderma and vasculitis.

Compositions for the Prophylaxis and/or Treatment of Autoimmune Diseases

The compositions for immunomodulation of autoimmune diseases comprise an agent that antagonizes the activity of FSTL-1. Examples of such agents include: antibodies and fragments thereof, soluble FSTL-1 receptor molecule, small molecule, antisense RNA and RNAi. In one aspect, the composition comprises an antagonist to FSTL-1 wherein the antagonist is capable of reducing or partially inhibiting or completely inhibiting the activity of FSTL-1. In a preferred embodiment, the antagonist is an antibody to FSTL-1.

Antibodies to FSTL-1

In accordance with the present invention, anti-FSTL-1 antibodies may be polyclonal or monoclonal; may be from any of a number of human, non-human eukaryotic, cellular, fungal or bacterial sources; may be encoded by genomic or vector-borne coding sequences; and may be elicited against native or recombinant FSTL-1 or fragments thereof with or without the use of an adjuvant, all according to a variety of methods and procedures well-known in the art for generating and producing antibodies. Generally, neutralizing antibodies against FSTL-1 (i.e., those that inhibit biological activity of FSTL-1 with regard to its pro-inflammatory role) are preferred for therapeutic applications, while non-neutralizing antibodies may be suitable for diagnostic applications. Examples of such useful antibodies include but are not limited to polyclonal, monoclonal, chimeric, single-chain, and various human or humanized types of antibodies, as well as various fragments thereof, such as Fab fragments and fragments produced from specialized expression systems.

For example, to produce an FSTL-1 antibody, various host animals may be immunized by injection with an FSTL-1 product, or a portion thereof including, but not limited to, portions of the FSTL-1 in a recombinant protein. In some embodiments, host animals may include but are not limited to rabbits, mice, and rats. In other embodiments, adjuvants may be used to increase the immunological response, depending on the host species. Such adjuvants include, but are not limited to mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Additionally, monoclonal anti FSTL-1 antibodies may be prepared using any technique that provides for the production of antibody molecules by continuous cell lines in culture. Such techniques, include but are not limited to, the hybridoma technique originally described by Kohler and Milstein, 1975, *Nature,* 256:495-497, the human B-cell hybridoma technique (Kosbor et al., 1983, *Immunology Today,* 4:72, Cote et al., 1983, *Proc. Natl. Acad. Sci.,* 80:2026-2030) and the EBV-hybridoma technique (Cole et al., 1985, *Monoclonal Antibodies and Cancer Therapy*, Alan R. Liss, Inc., pp. 77-96). In addition, techniques developed for the production of "chimeric antibodies" (Morrison et al., 1984, *Proc. Natl. Acad. Sci.,* 81:6851-6855; Neuberger et al., 1984, *Nature,* 312:604-608; Takeda et al., 1985, *Nature,* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to FSTL-1.

In one aspect, antibodies to FSTL-1 are directed to various portions of the protein. FSTL-1 has been described to have five domains. As such, antibodies directed to these five domains can be made using methods generally known to one of skill in the art and tested for its ability to antagonize the activity of FSTL-1. Compositions comprising antagonists (e.g, antibodies) can include more than one antibody. For example, antibodies that bind to different domains of FSTL-1 are contemplated as the composition. One example of tests that can be done to assess the ability of an antibody to be antagonizing to FSTL-1 is to use the antibody either in vitro or in vivo and monitor its effects on IL-17 production or secretion. Examples of in vitro or in vivo experiments are detailed in the Examples section below. If the antibody reduces the ability of FSTL-1 to induce IL-17, then it is said to be a neutralizing antibody. The neutralizing antibody can also be tested in animal models of diseases (e.g., collagen-induced arthritis (CIA) for arthritis, experimental allergic encephalomyelitis (EAE) for multiple sclerosis, etc.).

Alternatively, another method for assessing the neutralizing ability of an antibody to FSTL-1 is to use an in vivo model. The intradermal paw injection model described in Example 6 can be used to assess the neutralizing activity of an anti FSTL-1 antibody. Neutralization is assessed by the inhibition of inflammation and synovitis following injection of FSTL-1 into the mouse paw. Likewise, inhibition of the FSTL-1-induced increase in IL-1β, TNF-α, and IL-6 expression in paw homogenates is used as an endpoint for antibody neutralization of FSTL-1 activity. The recombinant FSTL-1 can be pre-incubated with a neutralizing antibody prior to injection into the paw. A neutralizing antibody is expected to block local IL-1β, TNF-α, and IL-6 secretion and prevent or minimize mouse paw and inflammation and synovitis in response to FSTL-1 injections. Alternatively, an animal is injected with the neutralizing antibody prior to injection of FSTL-1 into the paw to neutralize FSTL-1 activity prior to its ability to enact its proinflammatory effect. In both approaches, successful neutralization of FSTL-1 activity occurs when the neutralizing antibody blocks or significantly decreases the proinflammatory activity of FSTL-1.

The present invention also provides for compositions, more particularly, pharmaceutical compositions, primarily antibodies or antibody fragments, which neutralize FSTL-1 or otherwise inhibit or antagonize its activity, thereby inhibiting or reducing inflammation. Alternatively, the compositions can comprise a soluble FSTL-1 receptor molecule, small molecule, antisense RNA or RNAi. Such compositions are useful, e.g. in treatment of inflammatory conditions associated with cytokines IL-1β, TNF-α, and IL-6, such as arthritis or sepsis. Soluble FSTL-1 receptors may be identified and isolated for use in the present invention, e.g. as described in U.S. Pat. No. 5,605,690 and WO 94/06476 for soluble TNFRs.

The invention also contemplates kits comprising a composition comprising FSTL-1 antagonist. The composition can include more than 1 antagonist. In a preferred embodiment, the FSTL-1 antagonist is an antibody to FSTL-1, more preferably a neutralizing antibody. More than 1 antibody can be included in the kit, for example, antibodies that bind to different domains of FSTL-1. The antibody can be in any state suitable for packing in a kit, such as lyophilized or resuspended in a pharmaceutically acceptable excipient. The kit can further comprise instructions for use, such as dosing regimen. The kit can further comprise adjuvants that can be used with the composition.

Methods of Using Antagonists for Autoimmune Diseases

Accordingly, the invention provides for methods for treating an autoimmune condition in an individual by antagonizing FSTL-1 activity in the individual. Such antagonization can include inhibition of FSTL-1 activity. The invention also provides for methods for delaying development of an autoimmune condition in an individual by antagonizing FSTL-1 activity in the individual. The invention also provides for methods for delaying development of an autoimmune condition in an individual by antagonizing FSTL-1 activity in the individual. This antagonization can also include inhibition of FSTL-1 activity.

These methods are practiced by administering to an individual a composition comprising an effective amount of FSTL-1 antagonist (e.g., neutralizing antibody) to inhibit or reduce FSTL-1 activity. The antagonist may be a small molecule, an antibody or antibody fragment, a soluble FSTL-1 receptor that prevents binding of FSTL-1 to its cellular receptor, an antisense RNA or RNAi. Preferably, the antagonist of FSTL-1 is an antibody or antibody fragment, more preferably a neutralizing antibody or antibody fragment that blocks or reduces the biological activity of FSTL-1 in vivo. Alternatively, the inhibitor is a soluble FSTL-1 receptor.

For treatment, the composition comprising an effective amount of FSTL-1 antagonist (e.g., neutralizing antibody) can be administered as a pharmaceutical composition by using a pharmaceutically acceptable excipient. More details are given below for pharmaceutical formulations. The administration can be once or repeatedly over a period of time or as needed as dictated by the appearance of symptoms associated with autoimmune disease. A physician or one of skill in the art can monitor the individual for progress during the course of the treatment.

In another aspect, the invention provides for methods of delaying development of autoimmune disease by administration of a composition comprising an effective amount of FSTL-1 antagonist. In some cases, the autoimmune disease is prevented from occurring at all. In other cases, the administration of the FSTL-1 antagonist ameliorates one or more symptoms associated with autoimmune disease.

In other aspects, the present invention provides a method for identifying an agent that inhibits FSTL-1 activity that comprises contacting the agent with a FSTL-1 protein or a FSTL-1 fragment and determining whether binding and/or modulation occurs. The agent is preferably an antibody or antibody fragment. More preferably, the antibody or antibody fragment neutralizes or inhibits FSTL-1 activity. Neutralization of FSTL-1 activity means that the activity of FSTL-1 is completely blocked, preferably in vivo. Inhibition of FSTL-1 activity means that the activity is at least partially blocked, preferably in vivo. Both are acceptable for in vivo use. Also contemplated is a soluble FSTL-1 receptor that neutralizes or inhibits FSTL-1 activity, by interfering with the binding of FSTL-1 to its cellular receptor.

Alternatively, the invention provides a method for identifying an agent that inhibits FSTL-1 expression and/or activity by contacting the agent with a cell that expresses and/or produces FSTL-1 in an amount sufficient to inhibit FSTL-1. The agent may be a small molecule, an antibody or antibody fragment, RNAi or an antisense RNA. Preferably, the inhibitory agent is an antibody or antibody fragment, more preferably a neutralizing antibody or antibody fragment.

In other embodiments, the present invention provides a method of screening for a agent that inhibits FSTL-1 activity, comprising: contacting a FSTL-1 protein or a FSTL-1 fragment with one or more candidate agents, wherein the FSTL-1 protein or FSTL-1 fragment has proinflammatory activity; and determining whether the compound inhibits the proinflammatory activity of the FSTL-1 protein or FSTL-1 fragment. The agent may be a small molecule, antibody or antibody fragment, soluble FSTL-1 receptor, antisense RNA, or RNAi. Preferably, the agent is an antibody or antibody fragment, more preferably a neutralizing antibody or antibody fragment. Alternatively, the agent is a soluble FSTL-1 receptor that inhibits binding of FSTL-1 to its cellular receptor.

Immunomodulation of Th17 Pathway By FSTL-1 Antagonists

Although it is to be understood that autoimmunity can arises from other causes other than dysregulation of the Th17 pathway, the autoimmune diseases can also involve the dysregulation of Th17 pathway. The biological effects involved in the dysregulation include, but are not limited to, the generation of an undesirable number of Th17 cells, the expression and/or production of IL-17, the expression and/or production of IL-23, the interaction between TGF-β and IL-6 to generate Th17 cells, the interaction of IL-23 with another protein to facilitate the proliferation of Th17 cells, and generally, the generation of Th17 cells from naive CD4+ cells.

As shown in the Examples, FSTL-1 can induce Th17 cells. The composition and methods of using FSTL-1 antagonists to impact the generation of Th17 cells are discussed in greater detail below, however a brief introduction to the Th17 pathway is given first.

Classically, CD4+ T cells have been divided into two distinct lineages on the basis of their cytokine production profile: cells of the T helper (Th)1 lineage evolved to enhance eradication of intracellular pathogens and are characterized by their production of interferon gamma. Cells of the Th2 lineage, which evolved to enhance elimination of parasitic infections, are characterized by production of IL-4, IL-5, and IL-13, which are potent activators of B-cell IgE production and eosinophil recruitment. Immune pathogenesis that results from dysregulated Th1 responses can promote tissue destruction and chronic inflammation, whereas dysregulated Th2 responses can cause allergy and asthma. Recent studies have suggested a greater diversification of the CD4 T-cell repertoire than that encompassed by the Th1/Th2 paradigm. This knowledge has forced a reassessment of the Th1 lineage in autoimmunity. New studies that link the cytokines IL-23 and IL-17 to immune pathogenesis previously attributed to the Th1 lineage have led to the delineation of a new effector CD4+ T-cell, referred to as Th17.

Experimental autoimmune encephalitis (EAE) and collagen-induced arthritis (CIA), two prototypical autoimmune mouse models, have been traditionally associated with dysregulated Th1 responses. An important basis for this association has been a number of studies that have described ablation of disease development in gene-targeted mice deficient in the p40 subunit of IL-12 or mice treated with neutralizing antibodies specific for IL-12p40. See, for example, Constantinescu, C. S., *J. Immunol.*, 161: 5097 (1998); Leonard, J. P., *J. Exp. Med.*, 181:381 (1995); and Segal, B M, *J. Exp. Med.* 187:537 (1998). With the description of a new IL-12 family member, IL-23 (See, e.g., Oppmann, B, *Immunity* 13: 715 (2000), which also has the p40 subunit but is paired with a distinct second chain (IL-23p19 instead of IL-12p35), it became apparent that this association should be revisited. In two landmark studies, Cua and co-workers found that mice deficient in the IL-23p19 subunit were resistant to EAE and CIA, whereas IL-12p35-deficient mice remained susceptible. See, for example, Constantinescu, C. S., *J. Immunol.* 161: 5097 (1998); Leonard, J. P., *J. Exp. Med.*, 181: 381 (1995); and Segal, B M, *J. Exp. Med.*, 187: 537 (1998).

A positive correlation was noted between the availability of IL-23 and the development of CD4 T cells that produced IL-17, a potent T-cell derived pro-inflammatory cytokine. See, e.g., Aggarwal, S., *J. Biol. Chem.*, 278: 1910 (2003) and Kolls, J. K., *Immunity*, 21:467 (2004). IL-17-deficient mice demonstrate impaired joint inflammation following type II collagen immunization. Nakae, S., *J. Immunol.*, 171: 6173 (2003). Furthermore, neutralization of IL-17 decreases disease severity and overexpression of IL-17 in the joints exacerbates disease. Lubberts, E., *J. Immunol.* 167: 1004 (2001). Thus, in at least some forms of autoimmunity, it is the IL-23-IL-17 cytokine axis, and not the IL-12-IFNγ axis, that is crucial for disease pathogenesis. In human arthritis, IL-17 and IL-23p19 are present in the sera, synovial fluids and synovial biopsies of rheumatoid arthritis (RA) patients, while both are absent in osteoarthritis (OA). Honorati, M. C., *Rheumatology* (Oxford), 40: 522 (2001); Kim, H. R., *Rheumatology* (Oxford), 46:57 (2007); and Kotake, S., *J. Clin. Invest.* 103: 1345 (1999). IL-17 activates RA synovial fibroblasts to synthesize IL-6 and IL-8. Hwang, S. Y., *Arthritis Res. Ther.*, 6:R120 (2004).

The differentiation of the IL-17 producing cells, now termed Th17 cells, was initially thought to be dependent on the presence, during antigen stimulation, of IL-23 produced by antigen-presenting cells. Further study demonstrated that IL-23 signaling is not required for Th17 commitment and IL-17 production, but instead is important for amplifying and/or stabilizing the Th17 phenotype in chronic inflammation. Th17 commitment and IL-17 production was found to depend on combined signaling by TGF-β and IL-6 but is independent of IL-23. Bettelli, E., *Nature* 441: 235 (2006); Veldhoen, M., *Immunity*, 24: 179 (2006). In 2006, Ivanov et. al. demonstrated that retinoic orphan receptor (ROR) gt is the key transcription factor for differentiation of Th17 cells and that both TGF-β and IL-6 together are required to upregulate RORgt and induce Th17 cells. Ivanov, II, *Cell*, 126: 1121 (2006). Linkage of Th17 differentiation to RORgt represents a major advance that should accelerate understanding of the signaling circuitry that specifies Th17 programming, including how Smad and STAT signals emanating from TGF-b and IL-6 receptors might cooperate to specify Th17 commitment.

Composition comprising antagonists to FSTL-1 have utility in affecting the regulation of the Th17 pathway. The examples below show that FSTL-1 induces Th17 cells and that the induction of Th17 cells requires the participation of IL-23. IL-23 alone will not induce the generation of Th17 cells. Thus, antagonists to FSTL-1 are useful for decreasing the number of Th17 cells and its downstream effects, e.g., secretion of IL-17. As such, in one embodiment, the compositions comprising an antagonist to FSTL-1 have the ability to decrease the number of Th17 cells.

For autoimmune diseases that involve the dysregulation of Th17 cells, the compositions comprising antagonists to FSTL-1 can be used for both prophylaxis and treatment of autoimmune diseases. Compositions comprising antagonists to FSTL-1 and methods of use are described infra.

Immunomodulation of Cancer

The present invention demonstrates that FSTL-1 functions as a proinflammatory mediator that functions to upregulate proinflammatory cytokines, e.g. IL-6, TNF-α, and IL-1β. Furthermore, the inventors have also discovered that FSTL-1 also plays a role in the induction of IL-17 from T cells. The ability of FSTL-1 to function as a proinflammatory mediator suggests a possible role for its use in the field of cancer. The correlation between TNF-α and cancer is well-documented. Generally, it is known that tumor necrosis factors, such as TNF-α, are made by an individual's immune system in attempts to eradicate the cancer. As such, FSTL-1's ability to induce the production of TNF-α is helpful in an individual who is in needed of this type of inflammatory response, for example, in an individual combating cancer. Furthermore, the ability of FSTL-1 to induce the production of other proinflammatory cytokines, such as IL-6, IL-1β, and IL-17 is helpful in an individual who is in needed of this type of inflammatory response, for example, in an individual with one or more cancerous cells.

Accordingly, in one aspect, the invention provides for compositions and methods for inducing the production of proinflammatory cytokines in individuals in need thereof by the administration to the individual of a pharmaceutical composition comprising FSTL-1, or a fragment thereof, in an amount sufficient to induce the production of one or more proinflammatory cytokines. In one embodiment, the individuals are patients who have cancer or are suspected of having or getting cancer. In another embodiment, the proinflammatory cytokines are IL-6, TNF-α, IL-1β and IL-17.

In another aspect, the invention provides for compositions and methods wherein the pharmaceutical composition comprising FSTL-1, or a fragment thereof, is administered to individuals in need thereof in an amount sufficient to induce the production of tumor necrosis factors (e.g., TNF-α). In another aspect, the invention provides for compositions and methods wherein the pharmaceutical composition comprising FSTL-1 is administered to individuals in need thereof in an amount sufficient induce the production of IL-6. In another aspect, the invention provides for compositions and methods wherein the pharmaceutical composition comprising FSTL-1 is administered to individuals in need thereof in an amount sufficient to induce the production of IL-1β. In another aspect, the invention provides for compositions and methods wherein the pharmaceutical composition comprising FSTL-1 is administered to individuals in need thereof in an amount sufficient induce the production of IL-17.

The administration of the FSTL-1 or a fragment thereof to an individual is therefore used to induce an inflammatory immune response in the individual. The inflammatory immune response includes, but is not limited to, the production of proinflammatory cytokines such as IL-6, TNF-α, IL-1β and IL-17. As such, the invention provides for compositions and methods for inducing an inflammatory response in an individual in need thereof by administering to the individual a composition comprising FSTL-1 or a fragment thereof in an amount effective for inducing one or more of the proinflammatory cytokines. In one embodiment, there is one more cancerous cell in the individual. In another embodiment, the proinflammatory cytokine is selected from the group consisting of IL-6, TNF-α, TGF-β, and IL-17.

Without being bound by theory, since high metastatic tumors express higher levels of FSTL-1 than non-metastatic tumors, the immune system's surveillance system may recognize FSTL-1 as a metastatic phenotype and counter it by increasing TNF production as a defense mechanism against the tumors. As such, in one aspect, a pharmaceutical composition comprising FSTL-1 may be used for immunomodulation in individuals with cancer. In other aspects, the invention provides for compositions and methods for immunomodulating an individual's inflammatory condition wherein the inflammatory condition is cancer. In one aspect, the immunomodulation can be practiced by administering to the individual an effective amount of a pharmaceutical composition comprising FSTL-1 that induces the production of TNF-α. In another aspect, the immunomodulation can be practiced by administering to the individual an effective amount of a pharmaceutical composition comprising FSTL-1 that induces the production of IL-6. In another aspect, the immunomodulation can be practiced by administering to the individual an effective amount of a pharmaceutical composition comprising FSTL-1 that induces the production of TGF-β. In another aspect, the immunomodulation can be practiced by administering to the individual an effective amount of a pharmaceutical composition comprising FSTL-1 that induces the production of IL-17. In another aspect, the immunomodulation can be practiced by administering to the individual an effective amount of a pharmaceutical composition comprising FSTL-1 that induces a combination of one or more of the following cytokines: IL-6, TNF-α, TGF-β, and IL-17.

The pharmaceutical composition of FSTL-1 (or a fragment thereof) can be purified FSTL-1 from any source or made recombinantly and then purified (as detailed in the examples). In the alternative, FSTL-1 can be produced as a result of gene therapy. One of skill in the art can readily determine the amount of the pharmaceutical composition of FSTL-1 for dosing by first using an animal model of cancer and then scaling it appropriately for use in a human. The animal model of cancer is specific for the type of cancer being targeted. For example, mouse models containing xenografts of prostate cancer could be used to determine an amount of FSTL-1 that would be needed to reduce the growth of prostate cancer cells. Generally, an effective amount of the pharmaceutical composition of FSTL-1 would result in the production of any one of the following proinflammatory cytokines: IL-6, TNF-α, TGF-β, and IL-17. Methods for measuring the levels of proinflammatory cytokines are disclosed herein and also known to one of skill in the art. In the context of observing cancerous or tumor cells, the following could also be monitored: retardation of growth of cancer cells, elimination of cancer cells, inhibition of cancer cell growth, decrease in tumor size, and retardation of metastasis.

Administration and Pharmaceutical Compositions

The compositions of the present invention may be administered to an individual either by itself (complex or combination) or in compositions where it is mixed with suitable carriers and excipients. In some embodiments, the compositions may be administered parenterally, such as by intravenous injection or infusion, intraperitoneal injection, subcutaneous injection, or intramuscular injection.

In still other embodiments, the compositions may be administered topically, such as by skin patch, to achieve consistent systemic levels of active agent. For example, the compositions may be formulated into topical creams, skin or mucosal patches, liquids or gels suitable for topical application to skin or mucosal membrane surfaces. In yet other embodiments, the compositions may be administered by inhaler to the respiratory tract for local or systemic treatment.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

Methods and Materials

Adenoviral Vectors

A recombinant, E1a-E3-deleted replication defective adenovirus type 5 (Ad5) vector encoding the mouse FSTL-1 gene (NCBI Nucleotide database accession number BC028921) was generated through Cre-lox recombination as described by Hardy et. al. S. Hardy et al., *Journal of Virology* 71: 1842 (1997). The control vector, Ad-BglII, is an E1a/E3-deleted replication-defective adenovirus type 5 lacking an insert. The vectors were grown in 293 cells and purified by CsCl gradient ultracentrifugation, dialyzed at 4° C. against sterile virus buffer, aliquoted, and stored at −80° C. FSTL-1 expression was verified by both RT-PCR and western blot from infected COS-7 cells.

Cell Transfection

U937 cells were electroporated with pRcCMV-hFSTL-1 using a BioRad Gene Pulser (BioRad, Hercules Calif.) according to the manufacturer's protocol. Cells were maintained in G418 selection media for a period of 3-4 weeks and clones were isolated.

Purification of FSTL-1

Recombinant FSTL-1 was produced in bacculovirus. This system has a number of advantages over bacterial production. First, analysis of the effects of FSTL-1 on macrophages can be confounded by the presence of bacterial endotoxin, and it is difficult to ensure complete removal of endotoxin from bacterial protein preparations. Second, FSTL-1 glycosylation sites might be important for function and glycosylation would not occur in bacteria. Third, bacculovirus allows large scale production sufficient for in vivo studies. The inventors have already engineered both the human and the mouse FSTL-1 into the bacculovirus expression system. Supernatants have been harvested and protein purified by affinity chromatography on rabbit anti-FSTL-1 IgG sepharose columns, with elution by pH 4 acetate. Purification is confirmed by gel electrophoresis and ELISA.

Histologic Analysis

Mouse knee joints were fixed in 10% neutral buffered formalin, decalcified, dehydrated in a gradient of alcohols, paraffin embedded, sectioned, mounted on glass slides, and stained with hematoxylin and eosin. For immunohistochemistry, knees were fixed in 2% paraformaldehyde, cut longitudinally with a scalpel blade, mounted onto a cork disk with a small drop of cryogel (Cancer Diagnostics, Birmingham, Mich.), and placed into liquid nitrogen cooled isopentane for 45 seconds. Seven μm sections were obtained using a cryostat. Slides containing knee sections were fixed with 2% paraformaldehyde for 20 minutes and washed with PBS followed by BSA buffer (0.5% BSA and 0.15% glycine in PBS). Slides were blocked for 45 minutes with a 1:20 dilution of normal donkey serum (Sigma, St. Louis, Mo.) in BSA buffer and washed 3× with BSA buffer. The primary antibody goat anti-mouse FSTL-1 (R&D Systems, Minneapolis, Minn.) diluted to 10 ug/ml in BSA buffer was added, incubated for 2 hours, and washed 3× with BSA buffer. The secondary antibody Alexa Fluor® 488 donkey anti-goat IgG (Molecular Probes, Eugene, Oreg.) diluted 1:500 in BSA buffer was added, incubated for 1 hour, washed 3× with BSA buffer, and 3× with PBS. The nucleus stain DRAQ5™ (Biostatus Limited, Shepshed Leicestershire, UK) diluted 1:1000 in PBS was added, incubated for 30 minutes and washed 3× with PBS. A cover slip containing a drop of gelvatol was added and slides were stored at 4° C. until observation with confocal microscope. For the double staining of fibroblast-like synoviocytes and FSTL-1, the primary antibody rat anti-mouse Thy 1.2 (Pharmingen, San Jose, Calif.) was included at the same time as the goat anti-mouse FSTL-1 at a concentration of 1.5 μg/ml. The secondary antibody Alexa Fluor® 594 donkey anti-rat IgG (Molecular Probes, Eugene Oreg.) was used at 1:1000 dilution. Appropriate isotype control primary antibodies were used each time immunohistochemistry was performed. Immunohistochemistry slides were observed using an Olympus Fluroview 500 (Olympus, Melville N.Y.) confocal microscope.

Quantitative Reverse Transcriptase-Polymerase Chain Reaction (RT-PCR)

Total RNA was isolated from COS-7 cells or frozen liver using Ambion's ToTALLY RNA™ Isolation Kit (Ambion, Austin Tex.) following the manufacturer's instructions. To remove possible genomic DNA contamination, RNA was treated with DNase I (Ambion, Austin Tex.). Complimentary DNA (cDNA) was synthesized with random hexamer oligonucleotides using Invitrogen's SuperScript™ II Reverse Transcriptase Kit (Invitrogen, Carlsbad, Calif.). PCR was performed in a LightCycler (Mx3000P Stratagene, La Jolla Calif.) using Brilliant® SYBR® Green QPCR Master Mix (Stratagene, La Jolla Calif.) according to the protocol (95° C. hot start for 10 minutes followed by 40 amplification cycles, denaturation at 95° C., primer annealing at 59° C., amplicon extension at 72° C.) using oligonucleotide primer sets for IL-1β, IL-6, and TNF. L. Overbergh et al., *Journal of Biomolecular Techniques* 14: 33 (2003). The copy number (number of transcripts) of amplified products was calculated from a standard curve obtained by plotting known input concentrations of plasmid DNA and normalizing to 18S ribosomal RNA.

Cytokine Analysis

Titers of IL-1β, TNF-α, and IL-6 were determined using commercial enzyme-linked immunosorbent assays (ELISA) according to the manufacturer's instructions (R&D Systems, Minneapolis, Minn.).

Induction and Assessment of CIA

Male DBA/1 mice, 6-10 weeks of age, were purchased from Harlan (Indianapolis, Ind.) and Jackson Laboratory (Bar Harbor, Minn.) and housed in the animal resource facility at the Children's Hospital of Pittsburgh Rangos Research Center (Pittsburgh, Pa.). Mice were treated by intra-venous injection with $1 \times 10^{10}$ particles of adenoviral vectors in 200 μl of phosphate buffered saline (PBS). CIA was induced by intradermal immunization with bovine collagen type II (Elastin Products, Owensville, Mo.) and a booster given 21 days later as previously described. Mice were evaluated for arthritis several times weekly using a macroscopic scoring system ranging from 0 to 4 (0=no detectable arthritis; 1=swelling and/or redness of paw or 1 digit; 2=2 joints involved; 3=3-4 joints involved; and 4=severe arthritis of entire paw and digits). The arthritic index for each mouse was calculated by adding the score of the 4 individual paws. The statistical significance of difference was determined using the Exact Wilcoxon Test. P values <0.05 were considered significant. Mice were sacrificed at various times and joints were used for histopathology, while livers were snap frozen and stored in a liquid nitrogen freezer.

Example 2

The Role of FSTL-1 in Arthritis

The cellular distribution of FSTL-1 in the joints of mice was examined by immunohistochemistry at various times during the course of arthritis (FIG. 1). Mouse knee joints were harvested from mice prior to immunization with type II collagen (day 0), during acute arthritis (day 28), or during late arthritis (day 49). Tissues were sectioned and stained for FSTL-1 and observed under a confocal microscope at 40× (panels A-C). Higher magnification (100×) views of day 28 synovium show CD90+ fibroblasts in red (D), FSTL-1 in green (F) and co-localization of FSTL-1 with fibroblasts, indicated by the arrows (E).

An increase in expression was observed in early CIA (day 28) whereas only minimal expression was observed in late CIA (day 49). The expression of FSTL-1 was shown to be localized to fibroblasts, as evidenced by CD-90 staining. No expression was observed in macrophages, neutrophils, or T cells.

Example 3

FSTL-1 Induces Secretion of Proinflammatory Cytokines from Fibroblasts and Macrophages Arthritic synovium contains large numbers of fibroblasts and macrophages that are centrally involved in joint destruction. After demonstrating that fibroblast-like synoviocytes over-expressed FSTL-1 during acute arthritis, the downstream effects of such overexpression on this cell phenotype were examined. Although unsuccessful at transfecting primary mouse or human synovial fibroblasts, the monkey kidney fibroblast cell line, COS-7, was stably transfected by electroporation.

Figure 2:
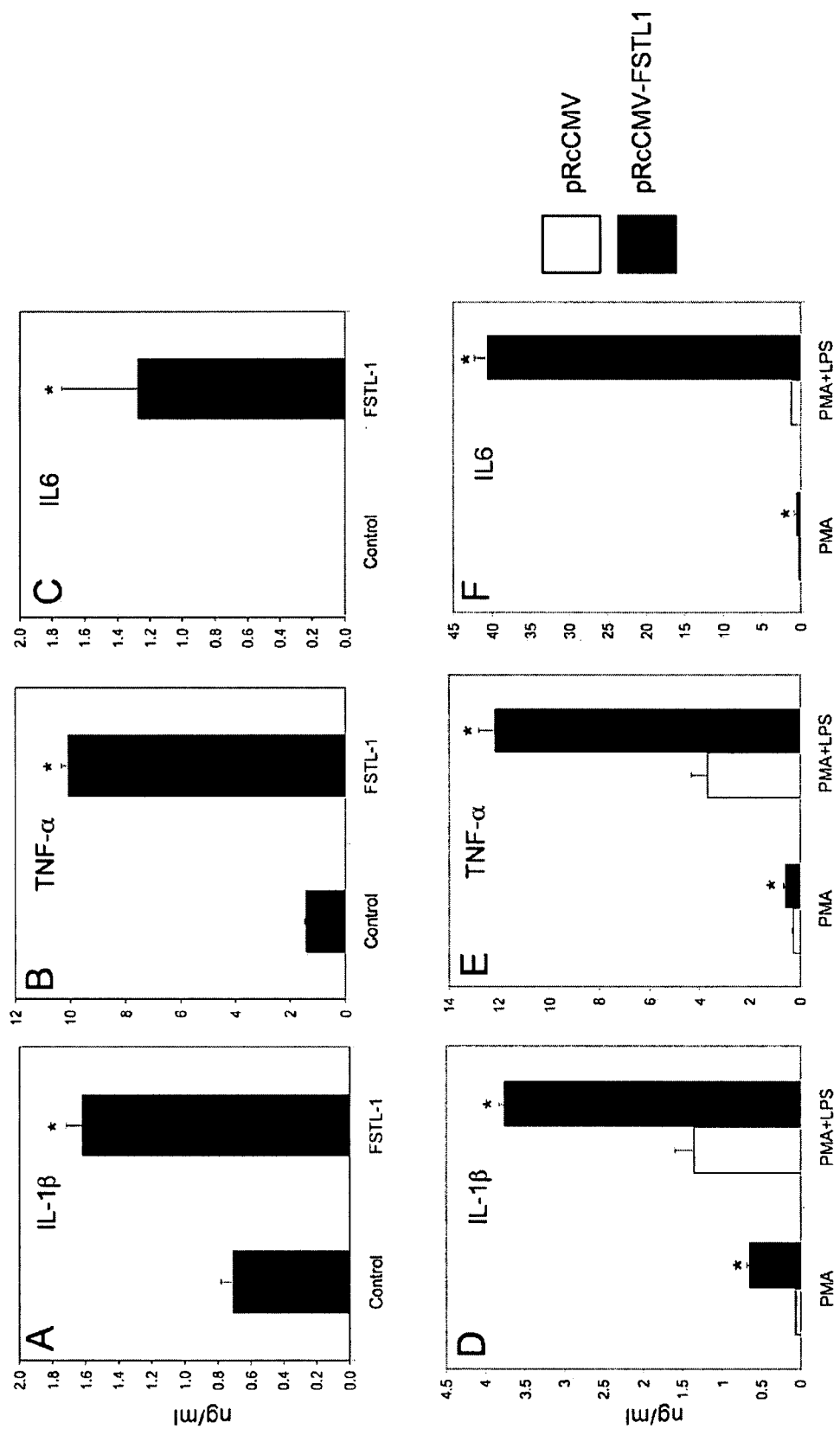
FIG. 2 shows that FSTL-1 induces secretion of proinflammatory cytokines from fibroblasts and macrophages.

FIG. 2 shows the results of experiments where monkey COS-7 fibroblasts were stably transfected by electroporation with a plasmid (pRcCMV) encoding the neomycin resistance gene with or without human FSTL-1. After selection for 4 weeks, RNA was extracted and assayed for IL-6 by real time PCR (A). Human U937 monocyte cells U937 cells were similarly transfected. After selection for 4 weeks, cells were stimulated with 10 ng/ml PMA in the presence or absence of 100 ng/ml LPS and assayed for IL-1β, TNF-α, and IL-6 (B-D respectively), *p<0.05.

Following transfection with human FSTL-1, COS-7 cells spontaneously expressed IL-6, while control cells transfected with the backbone plasmid did not (FIG. 2A). Human monocyte cell line, U937 was also stably transfected with human FSTL-1. Although these cells did not spontaneously produce inflammatory cytokines, addition of PMA to induce differentiation into macrophages led to secretion of IL-1β, TNF-α, and IL-6 (FIG. 2B-D). A substantial synergistic effect was observed upon addition of LPS, suggesting that FSTL-1 utilizes a distinct signaling pathway, different from the LPS receptor.

Example 4

FSTL-1 Induces Production of Proinflammatory Cytokines in vivo

Figure 3:
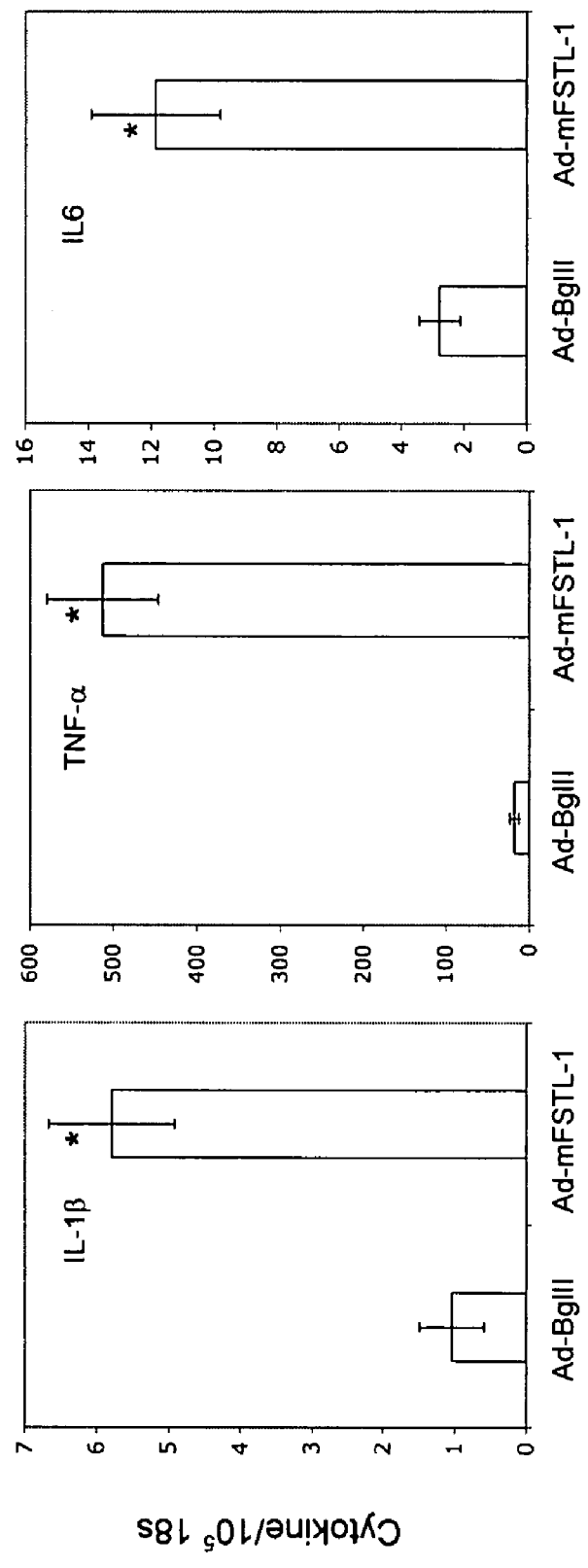
FIG. 3 shows that overexpression of FSTL-1 in liver induces gene expression of proinflammatory cytokines.

To determine the in vivo effects of over-expression of FSTL-1, DBA/1 mice were administered an adenovirus encoding either mouse FSTL-1 (Ad-mFSTL1) or a control virus lacking a transgene (Ad-BglII) by intravenous injection. FIG. 3 shows the results of experiments where mice were injected i.v. with $1 \times 10^{10}$ particles of either Ad-mFSTL-1 or Ad-BglII. Total RNA was isolated from liver 7 days later and amplified by real time PCR. The copy number of amplified product was calculated from a standard curve obtained by plotting known input concentrations of plasmid DNA. The copy numbers for IL-1β, TNF-α, and IL-6 of were normalized to the housekeeping gene 18s. Bars represent the mean and S.E.M. of 10 mice. *$p<0.05$.

Intravenous administration of adenovirus predominantly targets infection and gene expression to the liver. Seven days following adenovirus administration, livers were removed and analyzed for expression of IL-1β, TNF-α, and IL-6 by real time PCR. A pronounced increase was observed in mRNA for all 3 cytokines (FIG. 3), demonstrating that FSTL-1 upregulates their expression in vivo.

Example 5

FSTL-1 Exacerbates CIA

Figure 4:
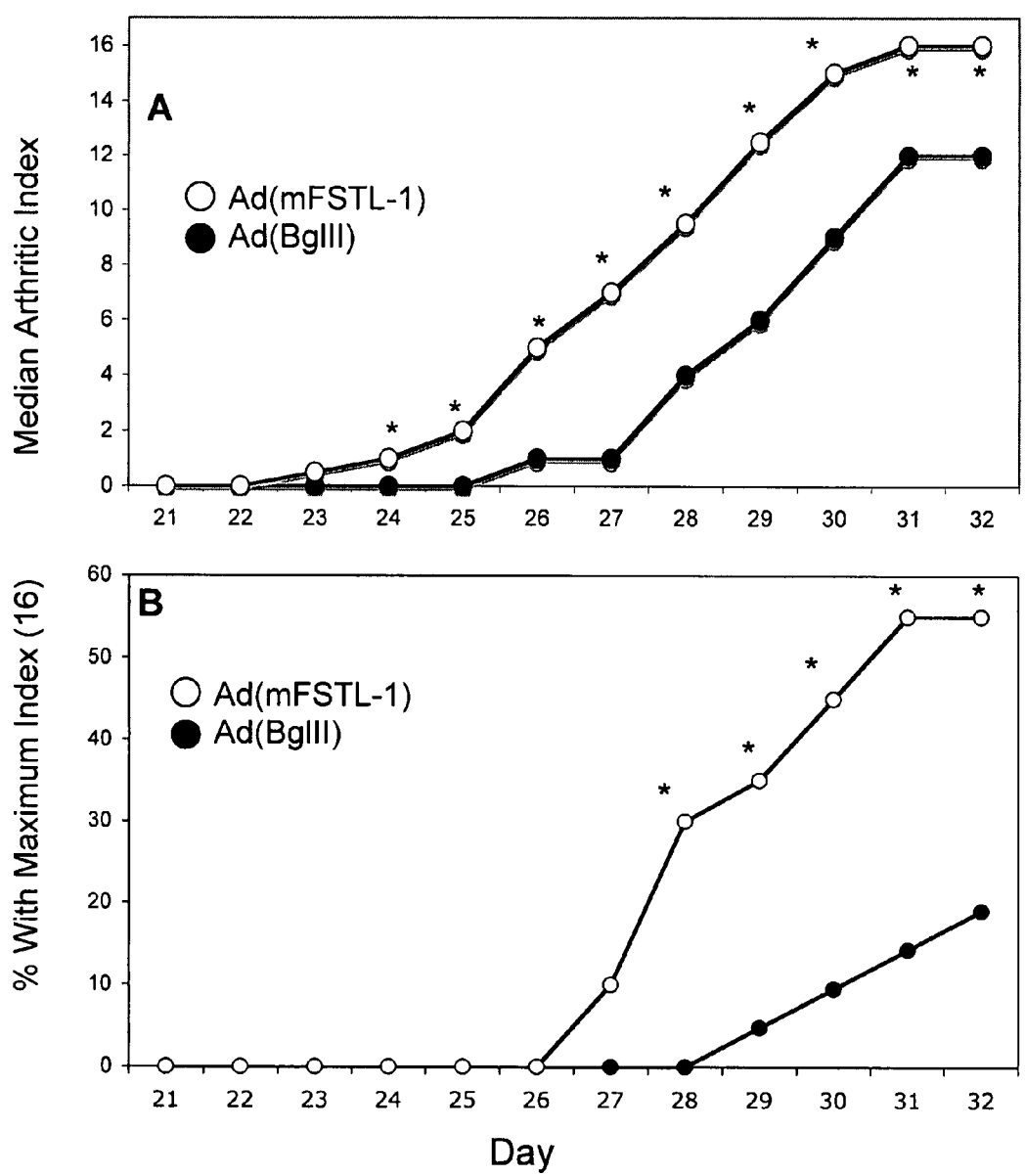
FIG. 4 shows that FSTL-1 exacerbates CIA.

To demonstrate that FSTL-1 functions as a proinflammatory mediator in arthritis, CIA was induced in DBA/1 mice by immunization with CII. FIG. 4 shows the results of experiments where mice were immunized with type II collagen on days 0 and 21. Mice were injected i.v. with $1 \times 10^{10}$ particles of adenovirus encoding either mouse FSTL-1 (Ad-mFSTL-1) or a control virus lacking a transgene (Ad-BglII) (20 mice per group) before the onset of arthritis (day 17). The arthritic index (A) and the % of mice with a maximum arthritis index (B) is shown. *$p<0.05$.

Mouse FSTL-1 was overexpressed prior to onset of arthritis by intravenous administration of Ad-mFSTL1. Control mice received a backbone adenovirus lacking a transgene (Ad-BglII). Severity of arthritis, as measured by the arthritic index, was significantly greater in mice receiving Ad-mFSTL1, compared to controls (FIG. 4A). Miyamae et al., *J. Immunol.* 177, 4758 (2006). There was also a significant increase in the percent of mice developing severe arthritis in the Ad-mFSTL-1 group (FIG. 4B).

Figure 5:
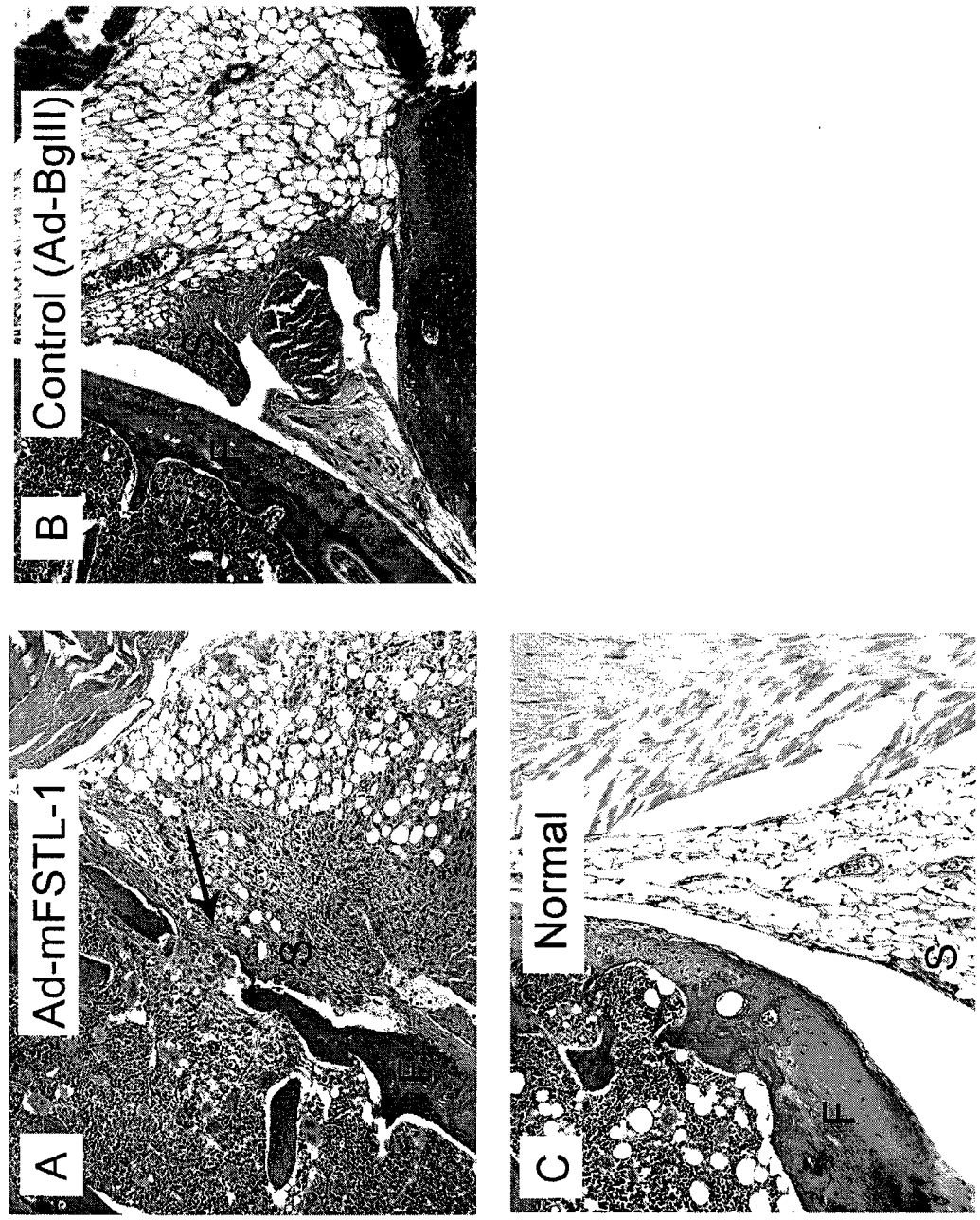
FIG. 5 shows that FSTL-1 exacerbates synovitis and joint destruction in CIA.

Histologic analysis correlated with the arthritic index scores (FIG. 5). Arthritic mice treated with either Ad-mFSTL1 (A) or with a control virus, Ad-BglII (B) were sacrificed on day 28, and knee joints were sectioned and stained with hematoxylin and eosin. An age-matched healthy control is shown in C. Severe inflammation of the synovium with invasion of cartilage and bone (arrow) is shown in A. F=femur, S=synovium (magnification ×200). Substantially more synovial inflammation, with infiltration of neutrophils and lymphocytes, and cartilage destruction was observed in mice administered FSTL-1.

Example 6

FSTL-1 Induces Spontaneous Inflammation and Synovitis

Figure 6:
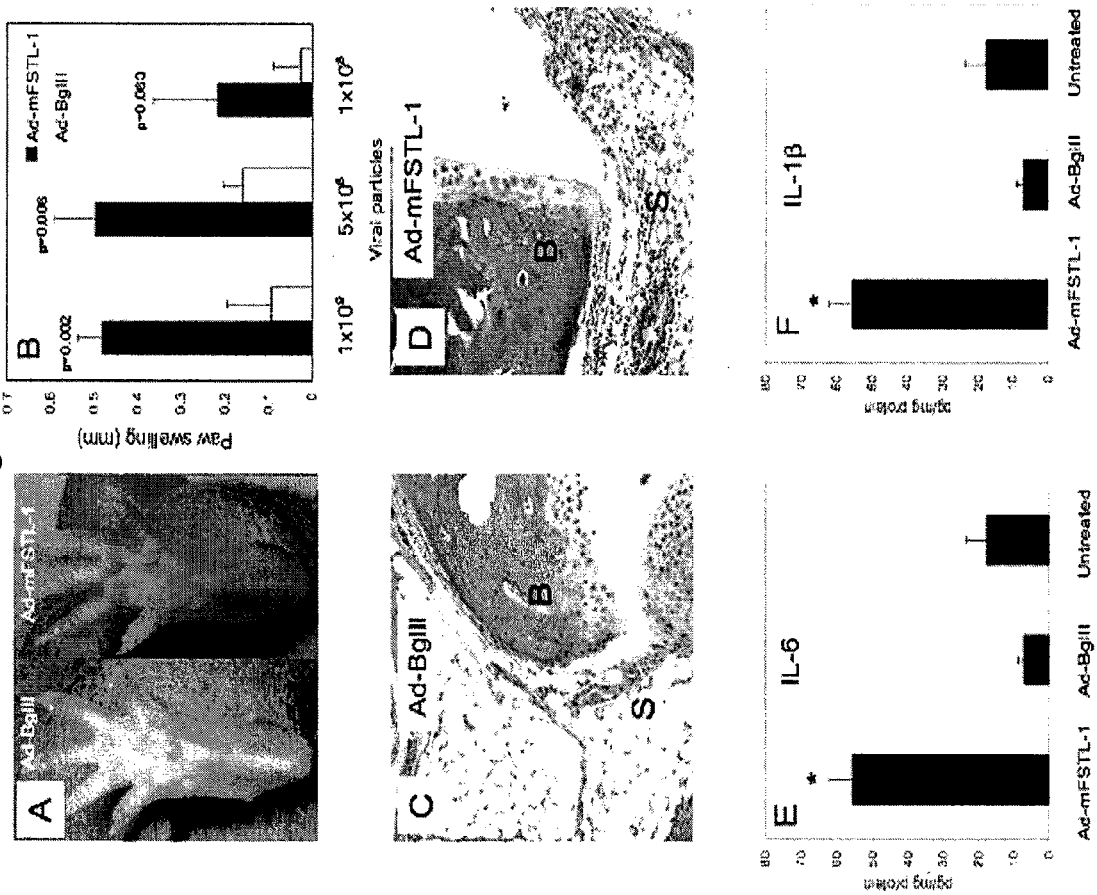
FIG. 6 shows that FSTL-1 induces spontaneous inflammation and synovitis.

To determine whether the observed proinflammatory effects of FSTL-1 required an anti inflammatory co-stimulus, such as immunization with CII, Ad-mFSTL-1 was injected intradermally into paws of unimmunized DBA/1 mice. FIG. 6 shows the results of experiments where the paws of healthy DBA/1 male mice were injected with Ad-mFSTL-1 or with a control virus, Ad-BglII, at viral titers ranging from $1 \times 10^9$ to $1 \times 10^8$ particles. Severe inflammation is observed in the Ad-mFSTL-1 group on day 8. Representative paws (at a titer of $1 \times 10^8$ particles) are shown in (A, C and D). (C) and (D) are at a magnification of ×100, where B=bone, S=synovium. Mean paw swelling and S.E.M. (n=8 paws) at each titer is shown in (B). Paw homogenates were assayed by ELISA for IL-6 (E) and IL-1β (F); data represents the mean and S.E.M. of 6 paws, except for untreated paws (n=3). *$p<0.05$.

Surprisingly, severe paw swelling and erythema was observed, beginning eight days after injection (FIG. 6A-B) and persisting for a week before subsiding. Histologic analysis revealed synovitis, with infiltration of inflammatory cells into the synovium and surrounding tissue (FIG. 6C-D). Protein homogenates from these paws had a significant increase in IL-6 and IL-1β, compared to control paws (FIG. 6E-F).

Example 7

FSTL-1 Neutralizing Antibody Inhibits CIA

A polyclonal neutralizing antibody against FSTL-1 was produced in rabbits, by immunizing the rabbits with full length recombinant follistatin-like protein 1 (FSTL-1), using methods known to one skilled in the art. Rabbit antiserum was assessed for its ability to antagonize and/or inhibit FSTL-1 bioactivity in vitro and in vivo and a polyclonal antibody against FSTL-1 was purified using affinity purification. ELISA assays were used to detect the secretion of IL-1β, TNF-α, or IL-6 following treatment of FSTL-1 by anti-FSTL-1 antibody. The measurement of paw swelling in response to the direct injection of recombinant FSTL-1 into mouse paws was used to monitor the in vivo effectiveness of anti-FSTL-1 antibody to antagonize or inhibit FSTL-1 activity. As provided above, a neutralizing antibody is an antibody or antibody fragment that blocks the bioactivity of FSTL-1.

Figure 7:
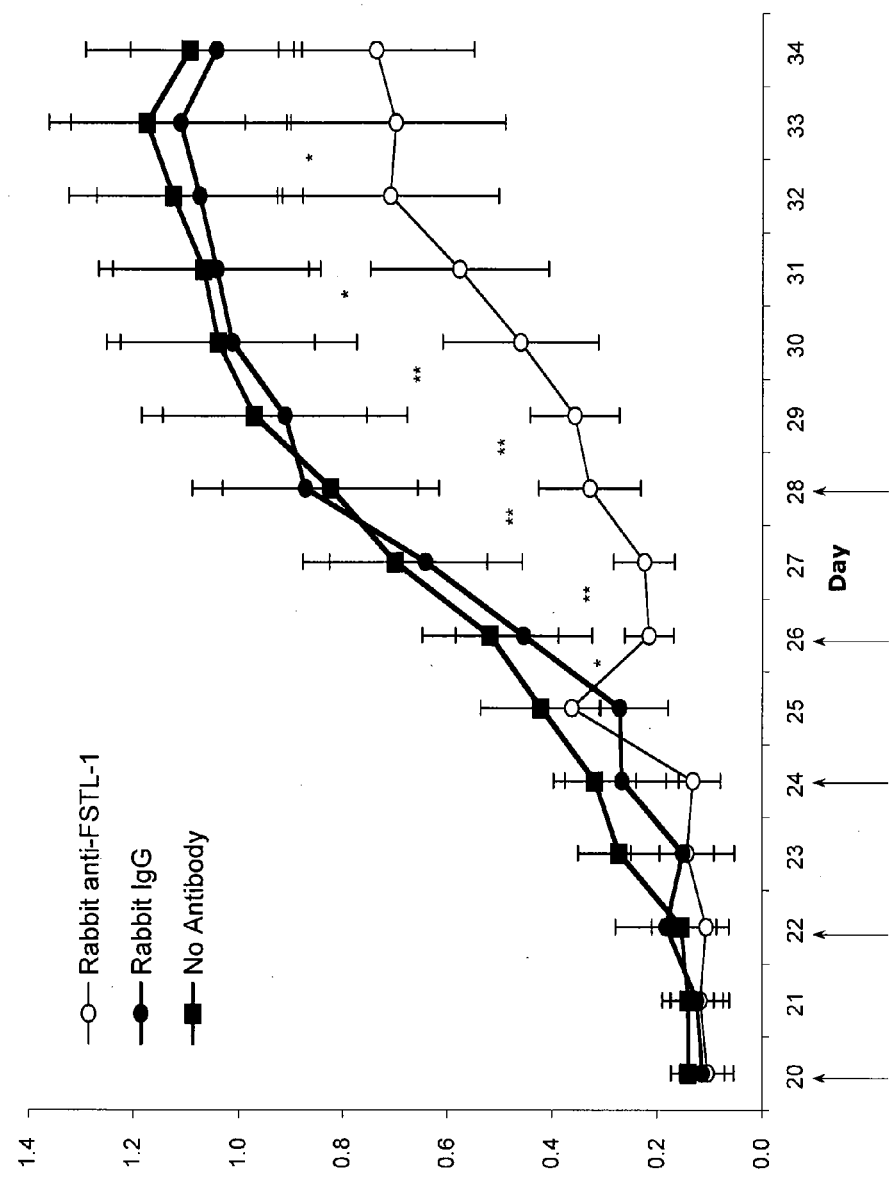
FIG. 7 shows in vivo results from administering a neutralizing antibody to FSTL-1 in a mouse model of arthritis (CIA). Paw swelling is indicated on the y-axis (measured in millimeters).

Mice were immunized with type II collagen on days 0 and 21. Mice were injected i.p. on the days indicated by the arrows in FIG. 7 with 200 µg of affinity purified rabbit anti-FSTL-1 IgG or polyclonal rabbit IgG as a control. A third group received no antibody (10 mice per group). Paw swelling (y-axis) was measured daily by a blinded observer. The single asterisk (*) datapoint indicates $p<0.05$ while a double asterisk (**) indicated $p<0.01$.

Example 8

In Vitro Neutralization

Figure 8:
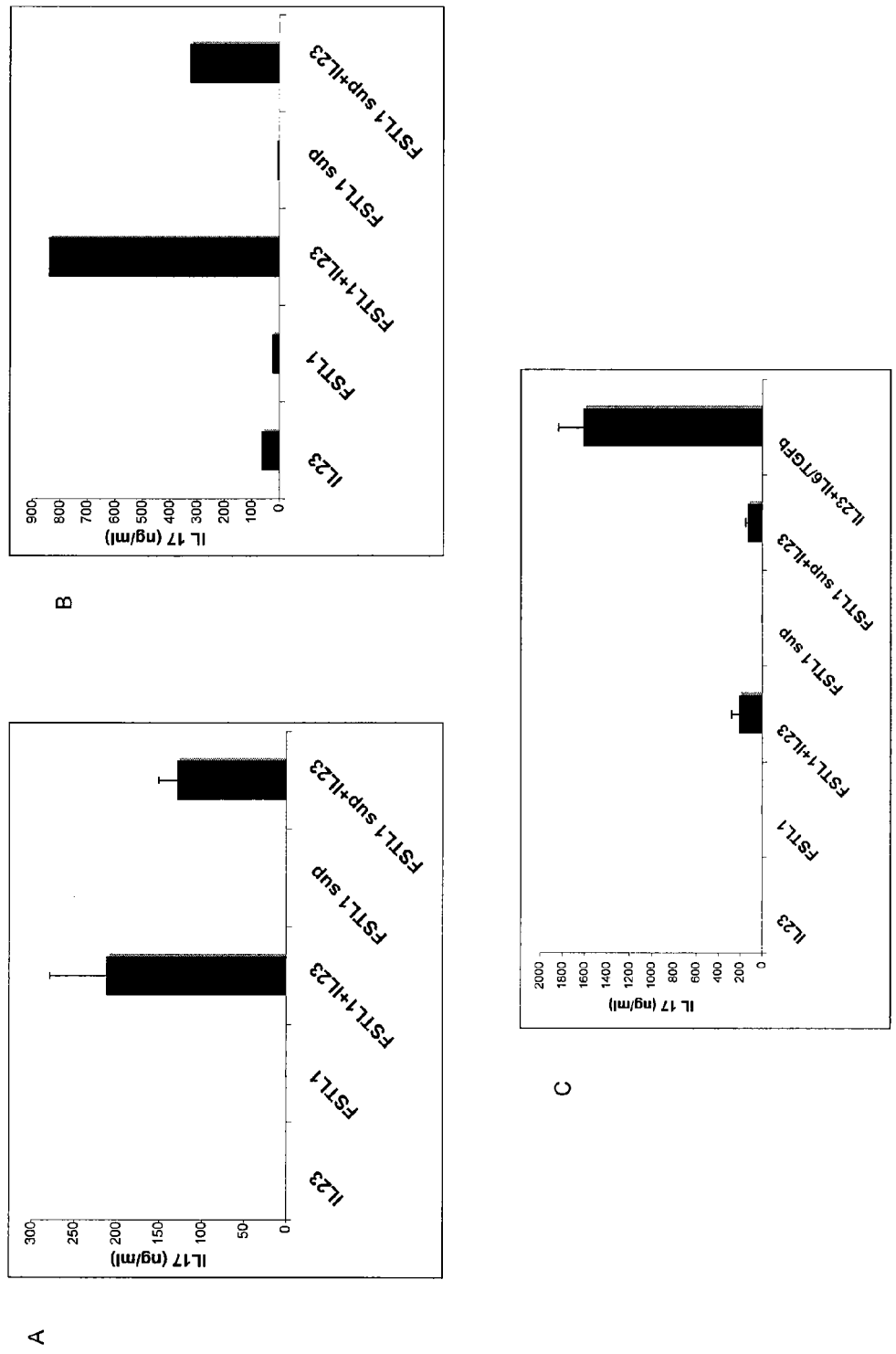
FIG. 8 are graphs that show that FSTL-1 induces the formation of Th17 cells. The amount of IL-17 from enriched spleen and lymph node cells incubated with IL-23 alone, FSTL-1 alone, FSTL-1+IL-23, FSTL-1 supernatant or FSTL-1 supernatant+IL-23 was measured by ELISA. In panel A, fresh OVA-pulsed APC (25,000 cells/well) were used. In panel B, anti-CD3/CD28 bead were used. Supernatants were harvested after 36 hours and assayed for IL-17. Panel C shows the same samples as panel A with the standard IL-6/TGF-β positive control group for perspective.

FSTL-1 protein, tagged to glutathione S-transferase (GST) or untagged, was produced in recombinant *E. coli* BL21 and purified over a glutathione Sepharose® column (if GST tagged) or by conventional column chromatography. As shown in FIG. 8, CD4+ T cells secreted IL-17 in response to FSTL-1 plus IL-23. The following approaches assessed the ability of a polyclonal anti-FSTL-1 rabbit, purified polyclonal anti-FSTL-1 antibody, an anti-FSTL-1 mAb, antiserum, or antibody fragment thereof to neutralize the bioactivity of FSTL-1. In one approach, recombinant FSTL-1 and IL-23 was pre-incubated with the neutralizing antibody. This combination was then exposed to CD4+ T cells to monitor the inhibition of IL-17 secretion therefrom using ELISA. In a second approach, CD4+ T cells were first exposed to the neutralizing antibody, then to the recombinant FSTL-1 and IL-23. The inhibition of secreted IL-17 from the treated CD4+ T cells was measured using ELISA. Bovine serum albumin or non specific immunoglobulin was used as a control for incubation on the effect of FSTL-1 on CD4+ T cells. Pre-incubation of FSTL-1 with a neutralizing antibody prevented the induction of IL-17 secretion following exposure of CD4+ T cells to the pretreated FSTL-1. Likewise, incubation of CD4+ T cells with a neutralizing antibody before exposing the cells to FSTL-1 and IL-23 also blocked the secretion of IL-17 in response to FSTL-1.

Example 9

FSTL-1 Induces Th17 Cells

This example shows the involvement of FSTL-1 in the Th17 pathway. DO11.10 spleen and lymph node cells were enriched for CD4+ T cells by positive selection with anti-CD4 magnetic microbeads (Miltenyi Biotec) and further purified by sorting for CD4+CD62L+CD25− cells on a Becton Dickenson cell sorter. $5 \times 10^5$ cells/well were plated in 48-well plates with irradiated syngeneic BALB/c spleen cells ($3.5 \times 10^6$ cells/well), to serve as APC. Cells were incubated for 5 days with OVA (5 mm), IL-2 (20 U/ml), anti-IFN-g (10 mg/ml), anti-IL-4 (10 mg/ml) and the following, as indicated in FIG. 8: IL-23 (10 ng/ml), FSTL-1 (1 mg/ml), FSTL-1-containing supernatant, IL-6 (10 ng/ml), and TGF-β (5 ng/ml). On day 3 the cells were split 1:2 and fresh cytokines and antibodies are added. On day 6, T cells were collected, counted, and plated at 60,000 cells/well in 96-well plates with either (A) fresh OVA-pulsed APC (25,000 cells/well) or (B) anti-CD3/CD28 beads (2 ml; Dynal)+IL-2 (10 U/ml). Supernatants were harvested after 36 hours and assayed for IL-17 by ELISA. (C) shows the same samples as in (A) with the standard IL-6/TGF-β positive control group for perspective. Data represents the mean and standard error of triplicate wells, except for the data depicted in (B).

Example 10

IL-23 Accelerates FSTL-1 Induced Paw Swelling

Figure 9:
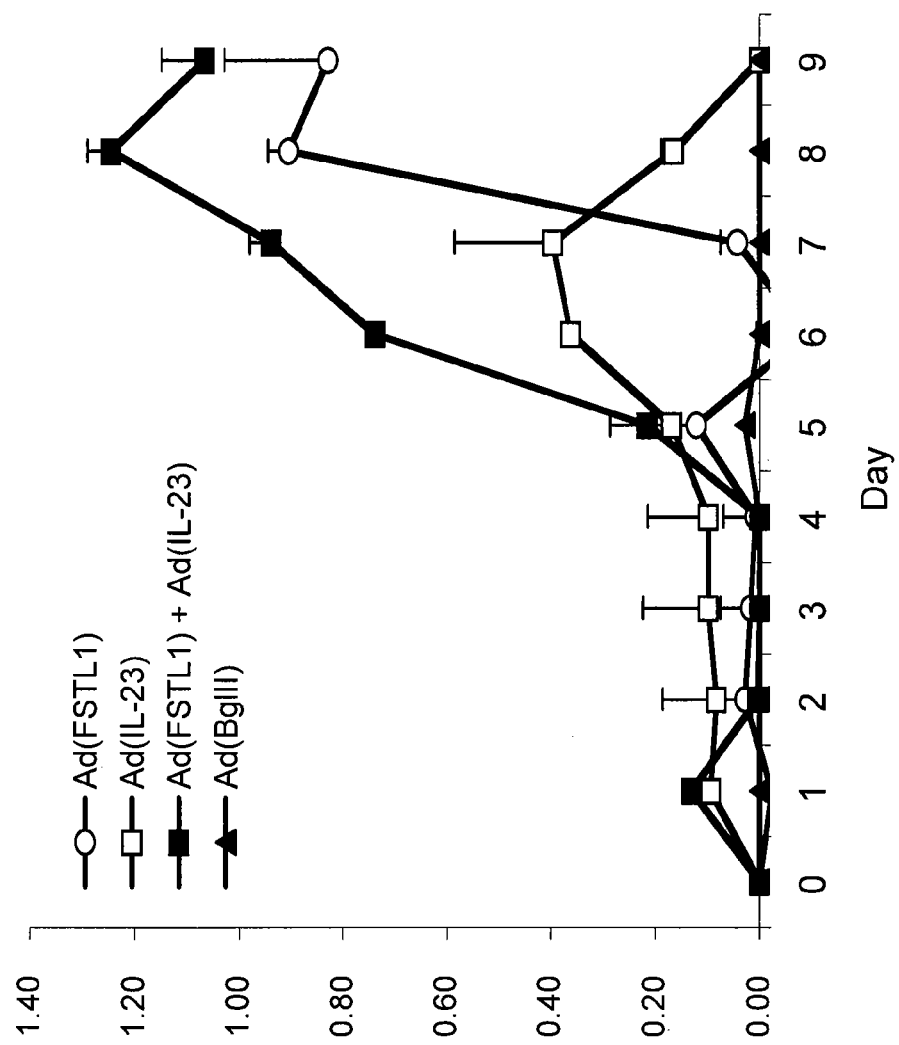
FIG. 9 show that IL-23 accelerates FSTL-1 induced paw swelling. The y-axis is paw swelling measured in millimeters.

This example shows that IL-23 accelerates FSTL-1-induced paw swelling. Hind paws of DBA/1 male mice were injected on day 0 with $5 \times 10^8$ Ad(FSTL-1) and/or $5 \times 10^8$ Ad(IL23). Control mice received $1 \times 10^9$ Ad(BglII). Paw swelling was measured using calipers. The data represents two paws/group for each condition (1 mouse). As shown in FIG. 9, mice in which both FSTL-1 and IL-23 were expressed experienced an earlier paw swelling than FSTL-1, while IL-23 alone had only a transient and mild effect.

Example 11

Antagonism of FSTL-1 for Treating or Delaying Development of Autoimmune Diseases Antagonists to FSTL-1, such as antibodies and neutralizing antibodies and fragments thereof are used for binding to FSTL-1. The binding of FSTL-1 by antagonists results in the delaying the development of Th17 cells. In some cases, there is a partial inhibition of the development of Th17 cells. In other cases, there is a complete inhibition of the development of Th17 cells. Animals models of inflammation are used to show this biological effect. A mouse model of arthritis, collagen-induced arthritis, CIA, is used (as in the examples above) is used to determine effect of antagonizing FSTL-1 on Th17 cell development. Antagonists to FSTL-1 delay the development of arthritis and/or ameliorate the symptoms of arthritis.

Multiple sclerosis can also be delayed and/or treated by using an antagonist to FSTL-1. A mouse model of experimental allergic encephalomyelitis (EAE) is used to show that binding to FSTL-1 by an antagonist can reduce one or more symptoms associated with multiple sclerosis by reducing the number of Th17 cells being generated.

Similarly, using antagonists to FSTL-1 to reduce the number of Th17 cells being generated is used to delay the development of and/or treat asthma, inflammatory bowel disease and diabetes. For all of the above, a composition comprising an antagonist to FSTL-1 in a pharmaceutically acceptable excipient is used for administration to the individual for prophylaxis or treatment of arthritis, multiple sclerosis, asthma, inflammatory bowel disease and diabetes.

Example 12

Induction of Inflammatory Response with FSTL-1

This example is directed toward the induction of an inflammatory response in an individual by administration with FSTL-1 or a fragment thereof in a pharmaceutically acceptable excipient. FSTL-1 is either a recombinantly FSTL-1, a fragment thereof, or made as a result of gene therapy. FSTL-1 is used as a modulator of the inflammatory response in an individual in need thereof by administering FSTL-1 in a pharmaceutically acceptable excipient either locally or systemically in an amount that would induce the production of at least one proinflammatory cytokine, such as TNF-α, IL-6, IL-1β, or IL-17. An example of an individual who is in need of such administration is an individual has at least one cancerous cell in his body. In another embodiment, the individual has been diagnosed with cancer. Methods of detecting TNF-α, IL-6, IL-1β, or IL-17 are disclosed here and known to one of skill in the art.

In an alternative, the pharmaceutical composition comprising FSTL-1 or a fragment thereof is administered to an individual in need thereof in an amount sufficient to induce the production of TNF-α. In another alternative, the pharmaceutical composition comprising FSTL-1 or a fragment thereof is administered to an individual in need thereof in an amount sufficient to induce the production of IL-6. In another alternative, the pharmaceutical composition comprising FSTL-1 or a fragment thereof is administered to an individual in need thereof in an amount sufficient to induce the production of TGF-β. In another alternative, the pharmaceutical composition comprising FSTL-1 is administered to an individual in need thereof in an amount sufficient to induce the production of IL-17. Following the administration of any one or a combination of the above, the individual is then monitored for production of one or more of the following: TNF-α, IL-6, IL-1β, or IL-17. Monitoring for signs of reduction of cancerous cells can also be done using routine laboratory techniques and are generally known to physicians and others of skill in the art.

What is claimed is:

1. A method for treating arthritis in an individual comprising administering to the individual an effective amount of an anti-FSTL-1 antibody, or an antigen-binding fragment thereof, such that FSTL-1 activity is antagonized.

2. The method of claim 1, wherein the antibody is a neutralizing antibody.

3. The method of claim 2 wherein the neutralizing antibody ameliorates at least one symptom associated with arthritis when administered to an individual.

4. The method of claim 1, further comprising a pharmaceutically acceptable excipient.

5. The method of claim 1, wherein the antibody is a monoclonal antibody.

6. The method of claim 1, wherein the antibody is a human antibody.

7. The method of claim 1, wherein the antibody is a chimeric antibody.

8. The method of claim 1, wherein the antibody is a humanized antibody.

9. The method of claim 1, wherein the arthritis is rheumatoid arthritis.

* * * * *

UNITED STATES PATENT AND TRADEMARK OFFICE
CERTIFICATE OF CORRECTION

PATENT NO. : 7,972,599 B2
APPLICATION NO. : 11/688779
DATED : July 5, 2011
INVENTOR(S) : Rapahel Hirsch, Anthony D. Marinov and David C. Wilson Page 1 of 1

It is certified that error appears in the above-identified patent and that said Letters Patent is hereby corrected as shown below:

Item (73) Assignee: University of Pittsburgh of the Commonwealth System of Higher Education should read -- University of Pittsburgh-of the Commonwealth System of Higher Education --

Signed and Sealed this
Nineteenth Day of February, 2013

Teresa Stanek Rea
*Acting Director of the United States Patent and Trademark Office*